US00PP28234P3

(12) United States Plant Patent
Carrières

(10) Patent No.: US PP28,234 P3
(45) Date of Patent: Aug. 1, 2017

(54) APPLE TREE NAMED 'RS1'

(50) Latin Name: ***Malus domestica* (Borkh.)**
Varietal Denomination: RS1

(71) Applicant: Red Moon GmbH, Bozen (IT)

(72) Inventor: Jean-Luc Carrières, Montcuq (FR)

(73) Assignee: RED MOON GMBH, Bozen (IT)

( * ) Notice: Subject to any disclaimer, the term of this patent is extended or adjusted under 35 U.S.C. 154(b) by 0 days.

(21) Appl. No.: 14/757,216

(22) Filed: Dec. 7, 2015

(65) Prior Publication Data

US 2017/0164534 P1 Jun. 8, 2017

(51) Int. Cl.
*A01H 5/00* (2006.01)

(52) U.S. Cl.
USPC ..... Plt./161

(58) Field of Classification Search
USPC ..... Plt./161
See application file for complete search history.

*Primary Examiner* — Annette Para

(74) *Attorney, Agent, or Firm* — James A. Lucas; Driggs, Hogg, Daugherty & Del Zoppo Co., LPA

(57) ABSTRACT

A new apple tree is characterized by a semi upright plant habit. The fruit has a red skin over color and a red flesh color. The timing of the fruit ripening in France is late August to September.

5 Drawing Sheets

Latin name of the genus and species of the plant claimed: *Malus domestica* (Borkh.).
Variety denomination: 'RS1'.

STATEMENT REGARDING FEDERALLY SPONSORED RESEARCH OR DEVELOPMENT

None

BACKGROUND OF THE INVENTION

The present invention relates to a new and distinct cultivar of apple tree, botanically known as *Malus domestica*, and hereinafter referred to by the name 'RS1'.

The new apple variety 'RS1' originated from an open-pollination in Lot, France of *Malus domestica* 'Zwintcher CSR 18', (not patented), as the female, or seed parent, with an unknown selection of *Malus domestica*, as the male or pollen, parent. The new Apple tree was discovered and selected by the inventors as a single plant from within the progeny of the stated open-pollination in a controlled environment in Lot, France in 2000.

Asexual reproduction of the new apple tree by budding and grafting, since 2006 in Lot, France, has demonstrated that the new variety reproduces true to type with all of the characteristics, as herein described, firmly fixed and retained through successive generations.

SUMMARY OF THE INVENTION

The following characteristics of the new variety have been repeatedly observed and can be used to distinguish 'RS1' as a new and distinct cultivar of apple:

1. Semi-upright plant habit.
2. Skin over color.
3. Medium timing of fruit ripening.
4. Red flesh color.

BRIEF DESCRIPTION OF THE PHOTOGRAPHS

DETAILED BOTANICAL DESCRIPTION

Figure 1:
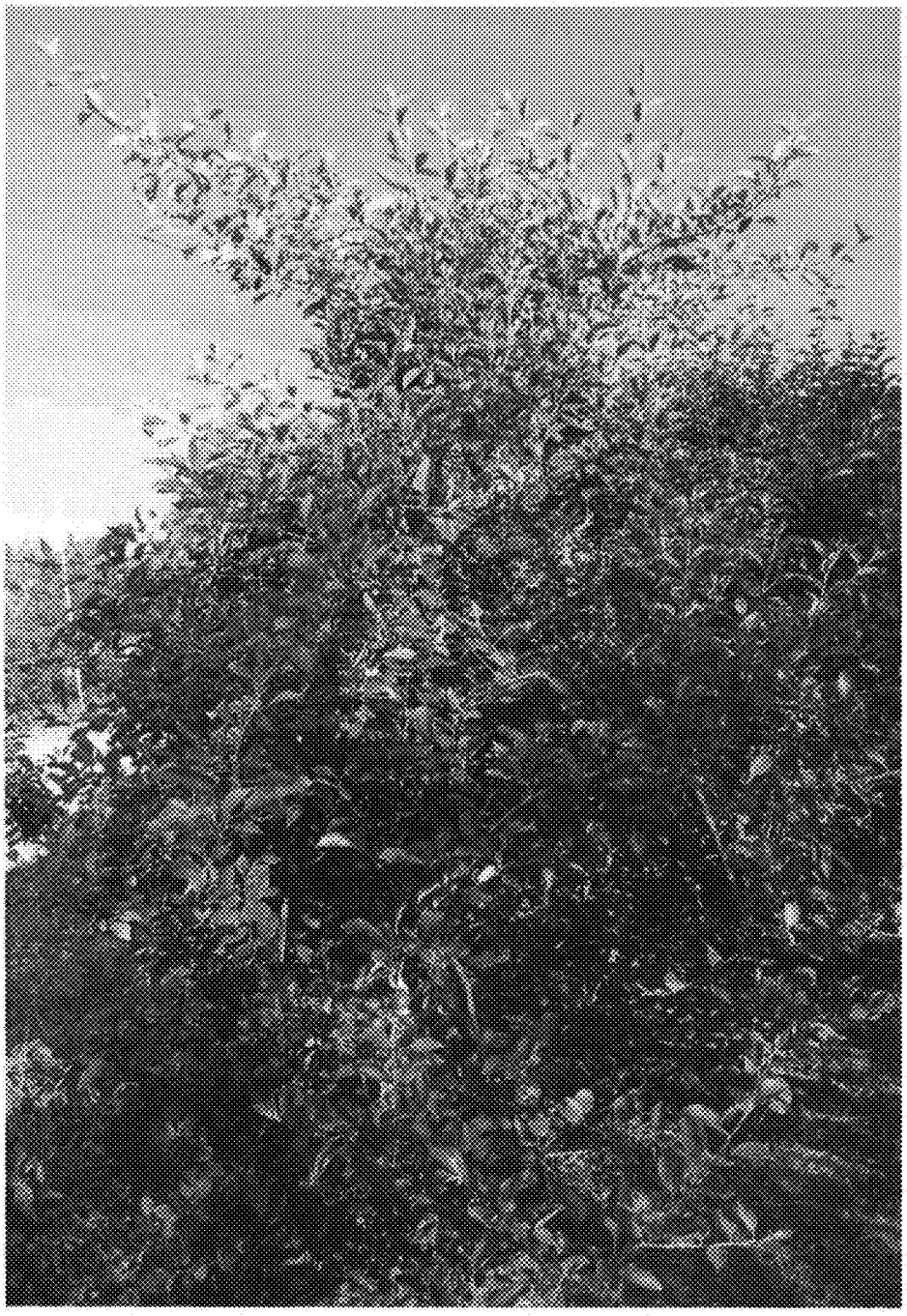
FIG. 1 shows the tree of the new variety.
Figure 2:
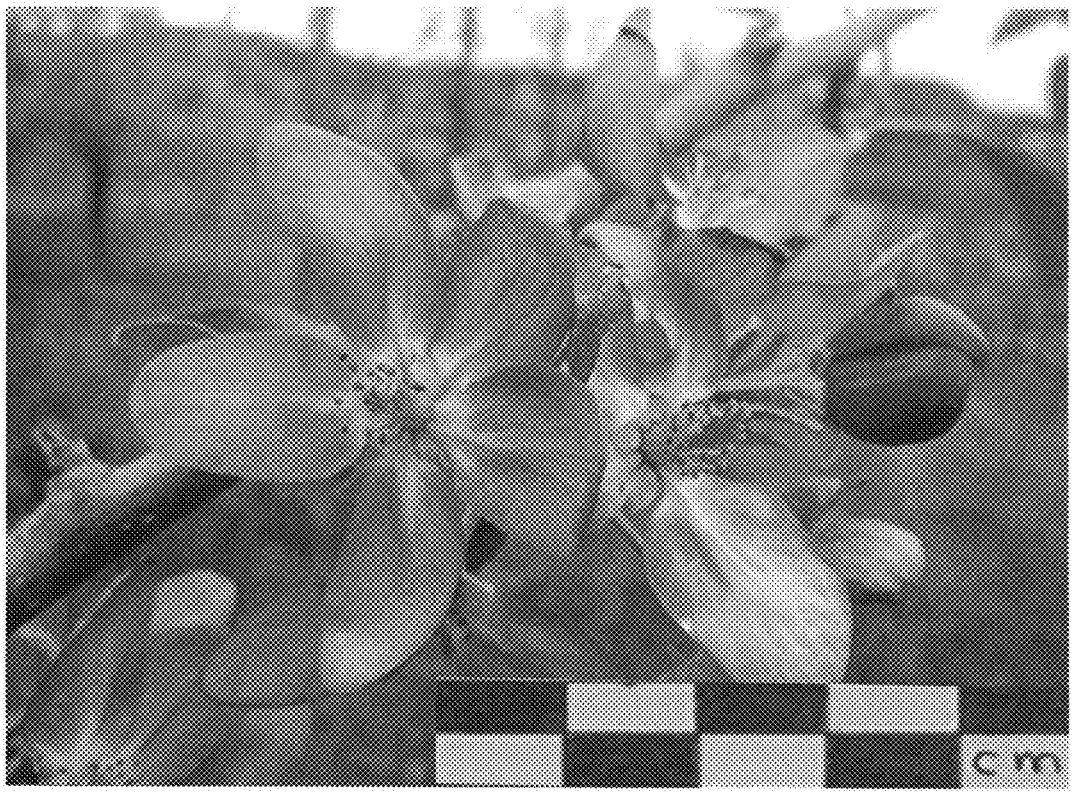
FIG. 2 shows the flower of the new variety.
Figure 3:
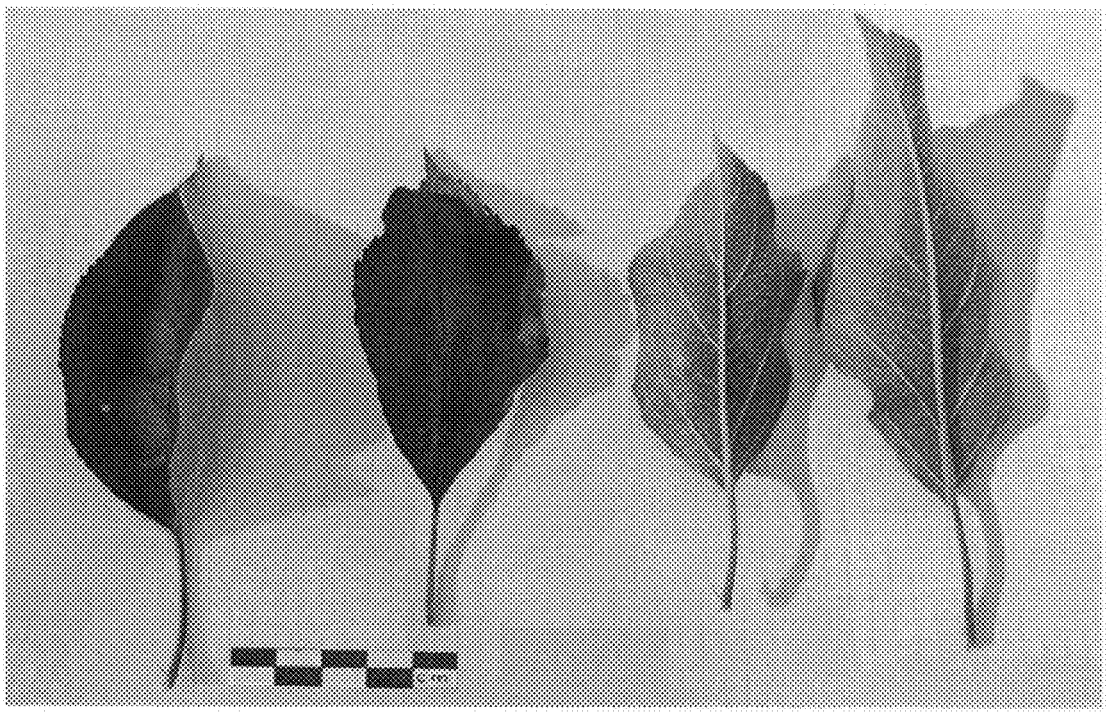
FIG. 3 shows the leaves of the new variety.
Figure 4:
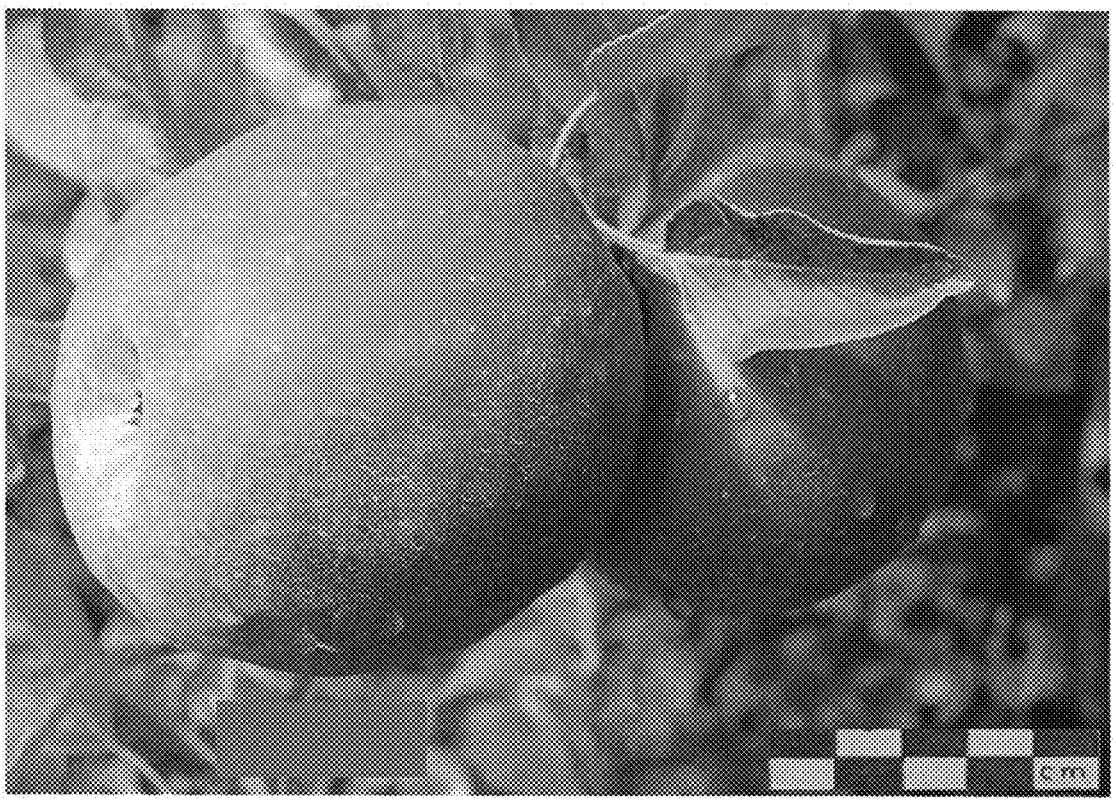
FIG. 4 shows the fruit of the new variety.
Figure 5:
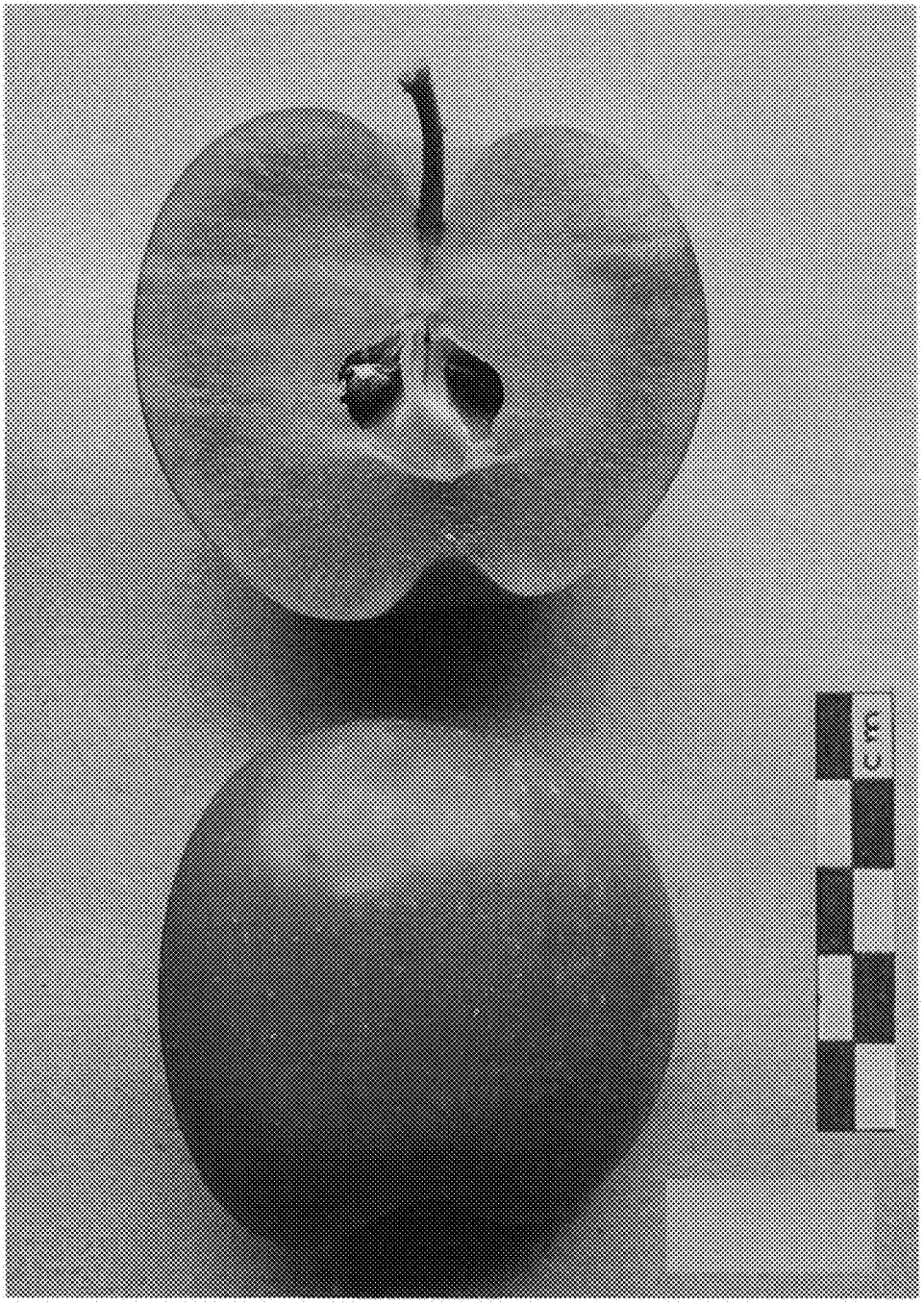
FIG. 5 shows the fruit section of the new variety.

The following detailed botanical description is based on observations of trees planted in 1995, and described during the 2013 and 2014 growing seasons at Lot, France. Color descriptions refer to The Royal Horticultural Society Colour Chart (1995). It should be understood that the characteristics described will vary somewhat depending upon cultural practices and climatic conditions, and can vary with location and season. Quantified measurements are expressed as an average of measurements taken from a number of individual plants of the new variety. The measurements of any individual plant, or any group of plants, of the new variety may vary from the stated average.

Botanical classification: *Malus domestica* Borkh cultivar 'RS1'.

Parentage:

*Female, or seed parent.*—*Malus domestica* 'Zwintcher CSR 18', not patented.

*Male, or pollen, parent.*—*Malus domestica* Unknown selection of *Malus domestica*, not patented.

Tree:

*Vigor.*—Vigorous.
*Habit.*—Semi-Upright.
*Size.*—Height: 3.0 m.
*Trunk.*—Diameter: 15-20 cm at 30 cm above graft union; bark texture smooth; color brown RHS N200C.
*Branches.*—1 m above graft union; length 150 cm; diameter 7.0 cm; crotch angle 75'; color light brown RHS 200D.

Dormant one year old shoot:

*Size.*—Diameter 4-5 mm; Length 20-30 cm
*Color.*—Brown RHS 200C.
*Internode length.*—2.0 cm.

*Pubescence*.—Strong.

*Lenticels*.—Size 1-2 mm, density 1-2/cm·sup·2.

Flowers:

*Bud*.—Quantity per spur 4 to 5; length 8-10 mm; shape globose; color red-purple RHS 63A.

*Petals*.—Quantity per flower 5; Margins free to touching; Apex shape round; Base shape round; Length 14-16 mm; Width 13-14 mm; upper surface color red RHS 42A; Lower surface color red RHS 43C.

*Flower*.—Diameter of fully open flower 2 cm; Quantity per cluster 5.

*Sepals*.—Quantity per flower 5; Shape triangular; color green RHS 135B.

*Pedicel*.—Length 19-21 mm; Diameter 2 mm; Color greyed-purple RHS 187A.

*Pistil*.—Length 13-14 mm; Color yellow-green RHS 145C.

*Anthers*.—Quantity per flower 16; length 2 mm; pollen color yellow RHS 12B.

*Stigma*.—Size 1 mm; Color RHS 11C.

*Style*.—Length 7 mm; color yellow-green RHS 145C.

*Bloom period*.—Early to Mid Season; first bloom April 8, full bloom April 12 at Lot, France.

Leaf:

*Attitude in relation to shoot*.—Outwards.

*Size*.—Length 10-11 cm; Width 5.0-6.0 cm; Length to Width Ratio 1.8-2.0.

*Margin*.—Serrate.

*Color*.—Upper green RHS 136A; lower surface green RHS 136A.

*Shape*.—Ovate; apex acuminate; base equilateral.

*Petiole*.—Length 1.5-2.0 cm; width 2 mm; color yellow-green RHS 143A.

Fruit:

*Size*.—Weight 120-150 g; diameter 75-80 mm.

*Fruit shape*.—Cylindrical.

*Position of maximum diameter*.—Top.

*Ribbing*.—Absent.

*Aperture of eye*.—Closed.

*Depth of eye basin*.—7-9 mm.

*Width of eye basin*.—30-35 mm.

*Stalk*.—Diameter 2.5 mm; length 15-20 mm; Color RHS 200B.

*Depth of stalk cavity*.—11-13 mm.

*Width of stalk cavity*.—20 mm.

*Lenticels*.—Size 0.5-0.7 mm; density 8-10/cm·sup·2.

*Bloom of skin*.—Absent.

*Greasiness of skin*.—Absent.

*Ground color of skin*.—Yellow-green RHS 45A.

*Over color of skin*.—Pink-Red RHS 60A.

*Amount of over color*.—90 percent.

*Pattern of over color*.—Solid flush with weakly defined stripes.

*Brix*.—12-15.

*Flesh*.—Texture juicy, firm, about 9.5 kg/cm·sup·2; color red RHS 52A.

*Seeds*.—Quantity per fruit 6-8; teardrop shape; color brown RHS 200B.

*Aroma*.—Medium.

*Harvest date*.—Late August to September.

*Susceptibility to known diseases/pests*.—Susceptible oidium.

Comparison of RS-1 with Seed Parent CSR-18

TABLE 1

| | RS-1 | CSR-18 |
|---|---|---|
| Flowering time: | Medium late | Late |
| Vigor: | Medium | Weak |
| Harvesting time: | Golden time | Golden + 4 week |
| Pressure kg/cm$^2$ | 8.9-9.3 | 5-6 |
| IR °Brix | 12.4-15.0 | 10.4 |
| Acidity | 11.3-13.9 g/L MA | NA |
| Density | 0.78 | NA |
| Vitamin C[1] skin | 18.5 ± 1.3 mg/100 g FW | NA |
| Storage | Good | Medium |

Xeleven is an unpatented variety differing from PRI 612-1 by having later harvesting, very firm flesh, better sugar level, a complex tropical flavor and very long storage. The patent status of PRI 612-1 and Golden are unknown.

TABLE II

| | Xeleven | PRI 612-1 | Golden |
|---|---|---|---|
| Flowering time: | Medium-Late | Medium | Medium |
| Vigor: | Medium | Strong | Medium |
| Harvesting time: | Golden + 5 week | Golden − 2 week | Mid September |
| Pressure kg/cm$^2$ | 9.9-10.3 | 8.5-9.5 | 6.6-7.0 |
| IR °Brix | 14.0-15.0 | 11.1-12.2 | 11.5-13.0 |
| Acidity | 7.8 g/L MA | 5.7-6.1 g/L MA | 3.8-5.1 g/L MA |
| Density | NA | NA | 0.78 |
| Vitamin C[1] flesh | NA | NA | 1.3 ± 03 mg/100 g FW |
| Storage | Very Good | Medium | Good |

What is claimed is:

1. A new and distinct apple tree substantially as shown and illustrated herein.

* * * * *